United States Patent
Satozono

(10) Patent No.: US 11,401,248 B2
(45) Date of Patent: Aug. 2, 2022

(54) LIQUID-LIQUID EXTRACTION METHODS FOR PURIFYING AND PRODUCING PURE THIOFLAVIN T BY MONITORING LIGHT EMISSION INTENSITY OF THIOFLAVIN T

(71) Applicant: HAMAMATSU PHOTONICS K.K., Hamamatsu (JP)

(72) Inventor: Hiroshi Satozono, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 475 days.

(21) Appl. No.: 15/762,166

(22) PCT Filed: Sep. 27, 2016

(86) PCT No.: PCT/JP2016/078416
§ 371 (c)(1),
(2) Date: Mar. 22, 2018

(87) PCT Pub. No.: WO2017/057344
PCT Pub. Date: Apr. 6, 2017

(65) Prior Publication Data
US 2018/0273497 A1 Sep. 27, 2018

(30) Foreign Application Priority Data
Sep. 29, 2015 (JP) .............................. JP2015-191309

(51) Int. Cl.
| | |
|---|---|
| G01N 33/52 | (2006.01) |
| G01N 33/68 | (2006.01) |
| C07D 277/66 | (2006.01) |
| C09B 57/00 | (2006.01) |
| C09K 11/06 | (2006.01) |

(52) U.S. Cl.
CPC ............ *C07D 277/66* (2013.01); *C09B 57/00* (2013.01); *C09K 11/06* (2013.01); *G01N 33/52* (2013.01); *G01N 33/6896* (2013.01); *G01N 2333/4709* (2013.01); *G01N 2800/2821* (2013.01)

(58) Field of Classification Search
CPC ....... G01N 33/52; G01N 33/68; C07D 277/66; C09B 57/00; C09K 11/06
USPC .......................................................... 436/86
See application file for complete search history.

(56) References Cited

U.S. PATENT DOCUMENTS

| | | | | |
|---|---|---|---|---|
| 412,978 | A | * 10/1889 | Rosenhek ............ | C07D 277/64 548/152 |
| 2,037,448 | A | * 4/1936 | Allemann ............ | C07D 277/66 548/152 |

(Continued)

FOREIGN PATENT DOCUMENTS

WO WO 2017-056758 A1 4/2017

OTHER PUBLICATIONS

Breffke, J., Dissertation 2014, '99 pages.*
(Continued)

*Primary Examiner* — Arlen Soderquist
(74) *Attorney, Agent, or Firm* — Faegre Drinker Biddle & Reath LLP

(57) ABSTRACT

The present invention relates to a method for purifying pure thioflavin T having a step of preparing a thioflavin T solution in which crude thioflavin T is dissolved in a polar solvent and a step of carrying out liquid-liquid extraction of the thioflavin T solution with a non-polar solvent.

3 Claims, 3 Drawing Sheets

(56) References Cited

U.S. PATENT DOCUMENTS

| | | | | |
|---|---|---|---|---|
| 2003/0187011 A1* | 10/2003 | Lashuel | ............... | A61K 31/473 514/284 |
| 2007/0235696 A1* | 10/2007 | Burrell | ................... | B01J 20/103 252/502 |
| 2018/0273498 A1* | 9/2018 | Oda | ..................... | C07D 277/66 |
| 2019/0056324 A1* | 2/2019 | Oda | ................... | G01N 21/6408 |

OTHER PUBLICATIONS

Kelenyi, G., Journal of Histochemistry and Cytochemistry 1967, 15, 172-180.*

Cundall, R. B. et al, Journal of Photochemistry 1981, 17, 369-376.*

Puchtler, H. et al, Histochemistry 1983, 77, 431-445.*

Maskevich, A. A. et al, Journal of Proteome Research 2007, 6, 1392-1401.*

Fodera, V. et al., Journal of Physical Chemistry B 2008, 112, 15174-15181.*

Sabate, R. et al, Journal of Structural Biology 2008, 162, 387-396.*

Nail, L. R. et al, Journal of Photochemistry and Photobiology A: Chemistry 2009, 204, 161-167.*

Hudson, S. A. et al, FEBS Journal 2009, 276, 5960-5972.*

Singh, P. K. et al, Physical Chemistry Chemical Physics 2011, 13, 8008-8014.*

Kuznetsova, I. M. et al., PLoS ONE 2012, 7, paper e30724, 8 pages.*

Liu, L. et al, Molecular Biosystems 2013, 9, 2512-2519.*

Enthammer, M. et al, Molecular Cancer Therapeutics 2013, 12, 2400-2414 and 35 pages of Supplimetary Information.*

Thioflavin T Product description posted by AAT Bioquest on Apr. 23, 2015, 2 pages, downloaded from https://aatbioquest.blogspot.com/2014/09/thioflavin-t.html?m=1.*

Labour, M.-N. et al, Acta Biomaterialia 2016, 37, 38-49.*

Martin, K., "Demystifying Material Grades for Your Laboratory" 8 pages, downloaded Nov. 3, 2020 from https://www.goldbio.com/articles/article/demystifying-material-grades-for-your-laboratory.*

"Immiscibility of Solvents" 2 pages, downloaded Nov. 2, 2020 from http://delloyd.50megs.com/MOBILE/immiscible.html.*

Groenning, Minna, "Binding mode of Thioflavin T and other molecular probes in the context of amyloid fibrils-current status," J Chem Biol., vol. 3, No. 1, 2010, pp. 1-18.

Freire, Sonia, et al., "Photophysical study of Thioflavin T as fluorescence marker of amyloid fibrils," Dyes and Pigments, vol. 110, 2014, pp. 97-105.

Hsu, Jack C.C., et al., "Thioflavin T and Its Photoirradiative Derivatives: Exploring Their Spectroscopic Properties in the Absence and Presence of Amyloid Fibrils," The Journal of Physical Chemistry B, vol. 117, 2013, pp. 3459-3468.

Levine III, Harry, "Thioflavine T interaction with synthetic Alzheimer's desease β-amyloid peptides: Detection of amyloid aggregation in solution," Protein Science, vol. 2, 1993, pp. 404-410.

Naik, L.R., et al., "Steady-state and time-resolved emission studies of Thioflavin-T," Journal of Photochemistry and Photobiology A: Chemistry, vol. 204, 2009, pp. 161-167.

Nishihama, Tadaaki, "Course of New Experimental Chemistry 1 Basic Operations I," The Chemical Society of Japan, Mar. 20, 1998, pp. 251-253 and pp. 291-295, including partial English translation.

Voropai, E.S., et al., "Spectral Properties of Thioflavin T and Its Complexes with Amyloid Fibrils," Journal of Applied Spectroscopy, vol. 70, No. 6, 2003, pp. 868-874.

International Preliminary Report on Patentability dated Apr. 12, 2018 for PCT/JP2016/078416.

\* cited by examiner

LIQUID-LIQUID EXTRACTION METHODS FOR PURIFYING AND PRODUCING PURE THIOFLAVIN T BY MONITORING LIGHT EMISSION INTENSITY OF THIOFLAVIN T

TECHNICAL FIELD

The present invention relates to a method for purifying pure thioflavin T. The present invention also relates to a method for producing pure thioflavin T, a composition containing thioflavin T, and a method for detecting amyloid.

BACKGROUND ART

Thioflavin T (ThT) is the most famous material known as a fluorescent staining pigment for amyloid, which is a special protein aggregate, and it is used for various studies.

It is known that two kinds of fluorescence are observed from a commercially available ThT reagent. Those two kinds of fluorescence are fluorescence having a peak wavelength near 440 nm (excitation wavelength is 350 nm, for example), and fluorescence having a peak wavelength near 480 nm (excitation wavelength is 430 nm, for example). It remains still unclear whether the fluorescence at the short wavelength side (fluorescence having a peak wavelength near 440 nm) originates from ThT or impurities in a ThT reagent.

For example, according to early studies, it has been reported in Non Patent Literature 1 that the impurities in a ThT reagent have an absorption for a wavelength of 350 nm and they are dissolved in hexane or cyclohexane. Meanwhile, according to Non Patent Literature 2, as the fluorescence of a wavelength 445 nm remains even after repetition of ThT purification (recrystallization), it is concluded as fluorescence originating from ThT and categorized as fluorescence which is emitted from part of a functional group forming ThT (local fluorescence). This local fluorescence hypothesis is supported by Non Patent Literature 3, and the physical and chemical origin of the hypothesis is discussed in the same document. Meanwhile, it is reported in Non Patent Literature 4 that ThT causes a photoreaction upon light illumination, and, by having an absorption band near a wavelength of 350 nm, it produces a photoreaction product which emits fluorescence with a wavelength of 450 nm, and it is described that the impurities in a ThT reagent originate from a photoreaction product of ThT.

CITATION LIST

Patent Literature

Non Patent Literature 1: J. Appl. Spectrosc., 2003, Vol. 70, No. 6, pp. 868-874
Non Patent Literature 2: J. Chem. Biol., 2010, Vol. 3, pp. 1-18
Non Patent Literature 3: Dyes Pigments, 2014, Vol. 110, pp. 97-105
Non Patent Literature 4: J. Phys. Chem. B, 2013, Vol. 117, pp. 3459-3468

SUMMARY OF INVENTION

Problems to be Solved by the Invention

The reason why it remains still unclear whether the fluorescence at the short wavelength side (fluorescence having a peak wavelength near 440 nm) originates from ThT or impurities in a ThT reagent is that, according to a technique of a related art, a ThT reagent having no fluorescence at the short wavelength side (pure ThT) cannot be obtained.

In consideration of the technical background which is described above, object of the present invention is to provide a method for obtaining a ThT reagent having no fluorescence at the short wavelength side, that is, a method for obtaining pure ThT.

Means for Solving the Problems

The present invention provides a method for purifying pure thioflavin T, including a step of preparing a thioflavin T solution in which crude thioflavin T is dissolved in a polar solvent and a step of carrying out liquid-liquid extraction of the thioflavin T solution with a non-polar solvent.

Because the method according to the present invention is to have liquid-liquid extraction with a non-polar solvent after preparing thioflavin T in a solution with polar solvent, a ThT reagent having no fluorescence at the short wavelength side (pure ThT) can be obtained. This also means that the fluorescence at the short wavelength side is not the fluorescence originating from ThT but the fluorescence originating from fluorescent impurities. Furthermore, according to studies conducted by the inventors of the present invention, it also becomes evident that the fluorescent impurities are produced again when ThT having no fluorescence at the short wavelength side is exposed to light (in particular, light with wavelength of 475 nm or lower). Namely, it is believed that the fluorescent impurities are a photoreaction product of ThT.

In the present specification, the "crude thioflavin T (crude ThT)" means a mixture of the aforementioned fluorescent impurities and ThT. Those conventionally referred to as "ThT" correspond to crude ThT of the present specification as they all include the fluorescent impurities that are described above.

In the present specification, the "pure thioflavin T (pure ThT)" means a ThT reagent having no fluorescence at the short wavelength side, and the "ThT reagent" has the same meaning as a molecular assembly containing ThT (composition). Thus, the "pure ThT" can be also recognized as a molecular assembly of ThT which includes substantially no fluorescent impurities or a molecular assembly which substantially consists of ThT. It is preferable that the "pure ThT" is a molecular assembly of ThT which includes no fluorescent impurities or a molecular assembly which consists of ThT.

Regarding the method described above, it is preferable that the step of liquid-liquid separation is carried out in a state in which light with a wavelength of 475 nm or lower is blocked. Accordingly, production of a new photoreaction product (fluorescent impurities) can be suppressed more, and thus pure ThT can be purified with even higher efficiency.

It is also possible that the method further includes a step of measuring light emission intensity of the fluorescence of a thioflavin T solution which has a peak wavelength near 440 nm and determining whether or not the measured light emission intensity reaches the background level, in which it is determined in the step of determination that the measured light emission intensity does not reach the background level, a step of liquid-liquid extraction of the thioflavin T solution is further carried out. Accordingly, it is possible to have a progress of the purification while monitoring the fluorescence originating from the fluorescent impurities.

The polar solvent may be a solvent selected from the group consisting of an aqueous solvent, methanol, ethanol, acetonitrile, and dimethyl sulfoxide, and a mixture solvent in which two or more types thereof are mixed with each other. Furthermore, it is also possible that the non-polar solvent is selected from the group consisting of hexane, heptane, octane, cyclohexane, toluene, and xylene, and a mixture solvent in which two or more types thereof are mixed with each other.

The present invention further provides a method for producing pure thioflavin T including a purification process for carrying out the above method for purifying pure thioflavin T.

The present invention further provides a composition containing thioflavin T in which light emission intensity of the fluorescence having a peak wavelength near 440 nm is at the background level.

Because the composition according to the present invention is a ThT-containing composition in which fluorescent impurities are not included, when it is used for fluorescent staining of amyloid, for example, the influence of the fluorescent impurities can be excluded so that the test results and diagnosis results can be obtained at higher precision. As such, the composition of the present invention is suitable for use in detecting amyloid. Namely, the present invention can be also recognized as a use or an application of a composition containing thioflavin T in which light emission intensity of the fluorescence having a peak wavelength near 440 nm is at the background level in detecting amyloid. Furthermore, the present invention also recognized as a composition containing thioflavin T for use in detecting amyloid in which light emission intensity of the fluorescence having a peak wavelength near 440 nm is at the background level.

The present invention still further provides a method for detecting amyloid, including a step of bringing a test sample into contact with a fluorescent reagent containing thioflavin T and a step of detecting fluorescence of the thioflavin T, in which the fluorescent reagent is the composition described above.

According to the method for detecting amyloid of the present invention, amyloid can be detected with higher precision from the viewpoint that the method uses a ThT-containing composition in which fluorescent impurities are not included.

The amyloid can be β amyloid. It is known that β amyloid is accumulated in a brain of a patient with Alzheimer's disease (senile plaque). Detection of β amyloid with high precision may greatly contribute to the elucidation of symptoms associated with Alzheimer's disease or the like.

Effects of the Invention

According to the present invention, it is possible to obtain pure ThT which cannot be obtained by a technique of a related art.

ThT is a fluorescent staining reagent which is the first choice for amyloid staining, and it is used not only for a study of amyloid but also for a pathological diagnosis of a disease related with amyloid. By using pure ThT for amyloid staining, the influence of fluorescent impurities on measurement results can be excluded, and thus test results and diagnosis results can be obtained with higher precision.

EMBODIMENTS FOR CARRYING OUT THE INVENTION

Hereinbelow, embodiments for carrying out the present invention are described in detail. However, the present invention is not limited to the embodiments that are given below.

[Thioflavin T]

Thioflavin T (ThT) is represented by the following chemical formula, and it is a known chemical compound also referred to as 4-(3,6-dimethyl-1,3-benzothiazol-3-ium-2-yl)-N,N-dimethylaniline chloride.

[Chem. 1]

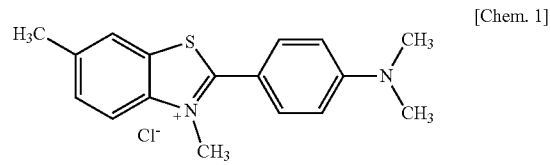

ThT exhibits fluorescence having a peak wavelength near 480 nm (excitation wavelength is 430 nm, for example). Meanwhile, upon illumination of light, ThT generates a photoreaction product (fluorescent impurities) which exhibits fluorescence having a peak wavelength near 440 nm (excitation wavelength is 350 nm, for example). Until now, it remains impossible to separate ThT from a mixture (crude ThT) of the fluorescent impurities and ThT.

The method for obtaining crude ThT is not particularly limited. It is possible to obtain it by purchasing a commercially available ThT reagent, or by synthesizing it according to a known method, for example.

[Method for Purifying Thioflavin T]

The method for purifying thioflavin T according to this embodiment includes a step of preparing a thioflavin T solution in which crude thioflavin T is dissolved in a polar solvent and a step of carrying out liquid-liquid extraction of the thioflavin T solution with a non-polar solvent. Furthermore, it is also possible to further include a step of measuring light emission intensity of the fluorescence of thioflavin T solution which has a peak wavelength near 440 nm and determining whether or not the measured light emission intensity reaches the background level. According to the purification method of this embodiment, pure ThT can be obtained.

Figure 1:
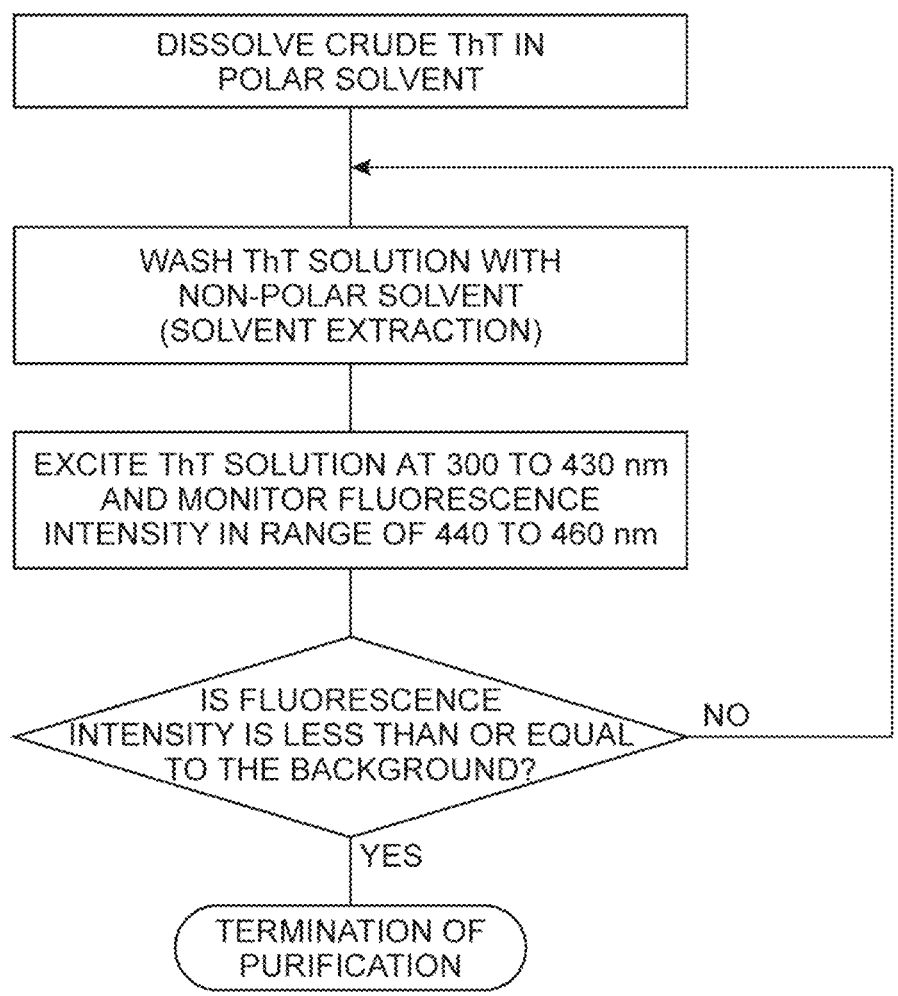
FIG. 1 is a flow chart illustrating the purification method according to one embodiment.

FIG. 1 is a flow chart illustrating the purification method according to one embodiment. Hereinbelow, one example of the purification method is described on the basis of FIG. 1.

The first step is a step of preparing a thioflavin T solution in which crude thioflavin T is dissolved in a polar solvent. The ThT solution can be prepared by dissolving crude ThT in a polar solvent, for example. Furthermore, when ThT is prepared as a solution in which it is dissolved in a polar solvent as it is synthesized or the like, the solution can be taken as a ThT solution.

As for the polar solvent, a solvent in which ThT can be dissolved can be used without any particular limitation. As for the polar solvent, a solvent with relative permittivity of 10 or more can be used, for example. Specific examples of the polar solvent include an aqueous solvent, methanol, ethanol, acetonitrile, dimethyl sulfoxide, and a mixture solvent in which two or more types thereof are mixed with each other. Examples of the aqueous solvent include water (including purified water used for pharmaceutical products, ion exchange water prepared by ion exchange, ultrafiltration, or the like, and ultra-pure water), a buffer solution like phosphate buffered physiological saline (PBS) and Tris-buffered physiological saline (IBS), and physiological saline. The polar solvent to be used is suitably selected depending on the use of ThT after the purification. For example, when ThT after the purification is used for detection of amyloid, an aqueous solvent is preferable as a polar solvent.

ThT concentration in the ThT solution is not particularly limited. However, it is generally within a range of 0.001 to 10 mmol/L. From the viewpoint of further suppressing new generation of a photoreaction product (fluorescent impurities) during the purification process, it is preferable to have low ThT concentration. ThT concentration is preferably within a range of 0.05 to 5 mmol/L. It is more preferably within a range of 0.025 to 2.5 mmol/L, and even more preferably within a range of 0.1 to 1 mmol/L. Furthermore, ThT concentration in the ThT solution can be set, depending on the use of ThT after the purification, such that it is not necessary to carry out again the dilution or concentration.

The second step is a step of carrying out liquid-liquid extraction of the thioflavin T solution with a non-polar solvent. According to this step, while ThT remains in the ThT solution, fluorescent impurities migrate from the ThT solution to a non-polar solvent so that the ThT solution is washed. The liquid-liquid extraction (liquid separation) can be carried out based on a known method. Specifically, the liquid-liquid extraction can be carried out by using a separating funnel or a liquid extraction device, for example.

As for the non-polar solvent, a solvent which does not dissolve ThT and has layer separation from a ThT solution can be used without any particular limitation. As for the non-polar solvent, for example, an organic solvent with relative permittivity of less than 10 can be used. Specific examples of the non-polar solvent include aliphatic hydrocarbons such as hexane, heptane, octane, or cyclohexane, aromatic hydrocarbons such as toluene, or xylene, and a mixture solvent in which two or more types thereof are mixed with each other.

The second step can be also a step in which, when an operation of having solute distribution by adding an un-extracted non-polar solvent to a ThT solution followed by sufficient mixing and having layer separation of the ThT solution (polar solvent layer) from the non-polar solvent layer is taken as one extraction operation, such extraction operation is repeated two or more times, for example. When the extraction operation is repeated two or more times, it is favorable that the ThT solution after layer separation is recovered, an un-extracted non-polar solvent is added to the recovered ThT solution, and the aforementioned operation is repeated.

Number of repeating the extraction operation can be suitably set as the number required for obtaining pure ThT depending on the type of polar solvent and non-polar solvent to be used and concentration of solute. The number required to obtain pure ThT can be set by confirming, according to repetition of the second step and third step described later, that the fluorescence intensity reaches the background level, for example. When water (pure water) is used as a polar-solvent and hexane is used as a non-polar solvent, for example, pure ThT can be obtained by repeating the extraction operation at least 10 times.

The third step is a step of measuring light emission intensity of the fluorescence (fluorescence intensity) of a ThT solution which has a peak wavelength near 440 nm. The fluorescence having a peak wavelength near 440 nm is specific to the fluorescent impurities.

In the third step, part of the ThT solution after liquid-liquid extraction (polar solvent layer) is collected to obtain a measurement sample, for example, and fluorescence intensity is measured. For measurement of the fluorescence intensity, for example, a fluorescence spectrophotometer, a fluorescence plate reader, or the like can be used. More specifically, a measurement sample is illuminated with light having a wavelength of 300 to 430 nm, and light emission in a wavelength of 440 to 460 nm (fluorescence) is measured accordingly. The wavelength of light for illumination can be suitably set within the aforementioned range. However, it is preferably a wavelength of 350 nm. The wavelength of fluorescence to be measured can be suitably set within the aforementioned range. However, it is preferably a wavelength of 440 nm.

In the fourth step, determination is made to see whether or not the light emission intensity measured in the third step reaches the background level. When it is determined that the measured light emission intensity does not reach the background level, the second step (step for liquid-liquid extraction) and the third step are (step for measuring light emission intensity) repeated additionally. When it is determined that the measured light emission intensity reaches the background level, the purification is terminated.

Furthermore, if the conditions for the liquid-liquid extraction (such as number of extraction, volume ratio of polar solvent/non-polar solvent, or the like) are set in advance, it is not necessary to perform the third step and the fourth step.

The "background level" means that the fluorescence intensity of a purified ThT solution is almost the same as the fluorescence intensity of a pure ThT solution. Determination of the "background level" can be carried out as described below, for example. Namely, in addition to the fluorescence intensity of a purified ThT solution at a wavelength of 440 nm, the fluorescence intensity at a wavelength of 480 nm is also measured, and the fluorescence ratio resulting from dividing the fluorescence intensity at a wavelength of 440 nm by the fluorescence intensity at a wavelength of 480 nm is obtained. When the fluorescence ratio is within a range of 0.4 to 1.0, it can be determined as "background level." Herein, it is preferably determined as "background level" when the fluorescence ratio is within a range of 0.5 to 0.9, and it is more preferably determined as "background level" when the fluorescence ratio is within a range of 0.6 to 0.8. Furthermore, more briefly, when the measurement value of fluorescence intensity which is measured in the third step does not decrease any further, it can be determined as "background level."

The ThT solution after completion of the purification can be used directly for next use. If necessary, it can be used as ThT powder for next use after removing the polar solvent. It can be also used for next use after ThT powder is dissolved again in any solvent.

The aforementioned purification method is preferably carried out in a state in which light with a wavelength of 475 nm or lower is blocked. Accordingly, production of new fluorescent impurities is suppressed so that the efficiency of the entire purification method can be enhanced more. It is possible that the entire process of the purification method is carried out in a light-blocked state. However, it is also possible that the process after the second step is carried out in a light-blocked state. The method for blocking light with a wavelength of 475 nm or lower can be suitably selected. Specifically, it is possible to carry out the purification operation under red light or carry out the purification operation in a (complete) light-blocked state.

[Method for Producing Thioflavin T]

The method for producing thioflavin T according to this embodiment includes a purification process for carrying out the method for purifying thioflavin T which has been described in the above. According to the production method of this embodiment, pure ThT can be obtained.

The production method according to this embodiment may also include, before the purification process, a synthesis process for synthesizing ThT, a dissolution process for dissolving crude ThT in a polar solvent, or the like. It is also possible that a packaging process for packaging the obtained pure ThT is included after the purification process. The packaging process may be a process in which the ThT solution is filled in a container like light-proof bottle (such as brown bottle), for example.

[Composition Containing Thioflavin T]

The composition containing thioflavin T according to this embodiment is a composition in which the light emission intensity of the fluorescence having a peak wavelength near 440 nm is at the background level. Namely, it is a composition which includes substantially no fluorescent impurities or a composition substantially consisting of ThT (molecular assembly). The composition according to one embodiment is a composition which contains thioflavin T and, when illuminated with light having a wavelength of 350 nm, has light emission intensity of the fluorescence having a wavelength of 440 nm at the background level.

The composition according to this embodiment can be any one of a liquid phase and a solid phase. From the viewpoint of suppressing generation of the fluorescent impurities, the composition according to this embodiment is preferably filled in a container like light-proof bottle (such as brown bottle).

The composition according to this embodiment can be obtained by the purification method or production method for ThT that are described above.

Because the composition according to this embodiment substantially contains no fluorescent impurities, when it is used for staining of amyloid, the influence of the fluorescent impurities on the measurement results can be excluded so that the test results and diagnosis results with even higher precision can be obtained. Thus, the composition according to this embodiment can be suitably used as a composition for use in detecting amyloid (fluorescent reagent for detecting amyloid).

[Method for Detecting Amyloid]

Amyloid represents a special aggregation state of a protein which has a specific β sheet structure. Depending on a difference in protein as a source, many types of amyloid are present. Namely, in the case of insulin, it is referred to as insulin amyloid. In the case of β2 microglobulin, it is referred to as β2 microglobulin amyloid, and in the case of amyloid β protein, it is referred to as β amyloid. Accumulation of amyloid in a human body may be a cause of a disease. For example, β2 microglobulin is related with dialysis amyloidosis, and amyloid β is related with Alzheimer's disease.

The method for detecting amyloid according to this embodiment can be carried out according to a common method except that the composition according to the present invention is used as a fluorescent reagent.

EXAMPLES

Hereinbelow, the present invention is described more specifically based on Examples. However, the present invention is not limited to the following Examples.

By dissolving 3.4 mg of ThT (manufactured by AAT Bioquest Inc., corresponds to the crude ThT in the present specification) in 20 mL of pure water, ThT solution was prepared.

Next, the ThT solution was added to a separating funnel, added with 50 mL of hexane, and mixed thoroughly to perform an extraction operation. After that, from a cock at the lower side of the separating funnel, the ThT solution was extracted. Part of the ThT solution was collected in a cuvette and used for measurement of fluorescence intensity with excitation wavelength of 350 nm and observation wavelength of 440 nm using fluorescence spectrophotometer RF-5000 (manufactured by SHIMADZU CORPORATION).

Figure 2:
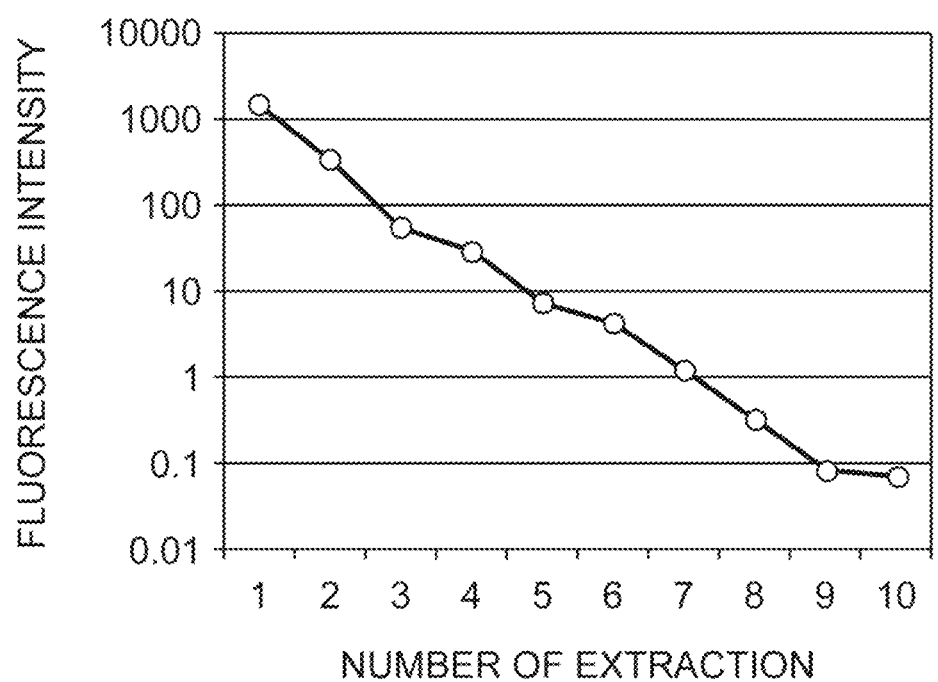
FIG. 2 is a drawing illustrating the relationship between the number of liquid-liquid extraction and fluorescence intensity.

The aforementioned extraction was repeated 10 times until the fluorescence intensity reaches the background level (measurement value of fluorescence intensity does not decrease any more). The relationship between the number of liquid-liquid extraction and fluorescence intensity is shown in FIG. 2. It was found that the fluorescence intensity reaches the background level at the $10^{th}$ extraction. Furthermore, the fluorescence ratio between the fluorescence intensity at observation wavelength of 440 nm and the fluorescence intensity at wavelength of 480 nm, which has been separately measured, was found to be 0.667. It can be determined as the background level also from this fluorescence ratio.

Figure 3:
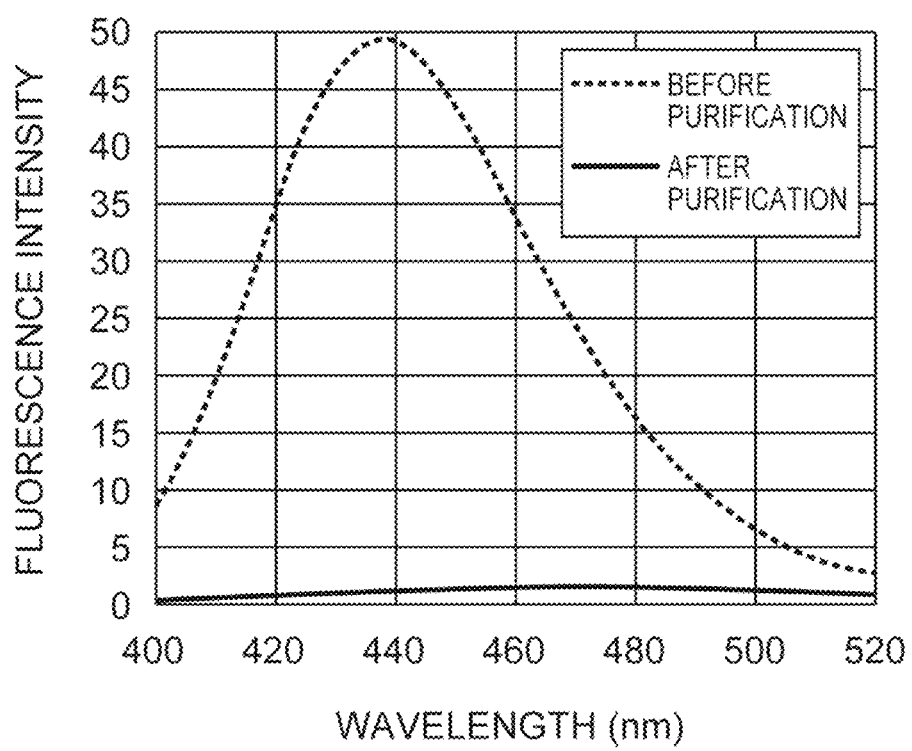
FIG. 3 is a drawing in which fluorescence spectra of ThT solution before and after the purification are compared to each other.

Fluorescence spectrum of the ThT solution after the purification is shown in FIG. 3. For comparison, fluorescence spectrum of the ThT solution before the purification is also shown. As it is evident from FIG. 3, the ThT solution after the purification showed complete loss of the fluorescence which has a peak wavelength near 440 nm so that only the fluorescence which has a peak wavelength near 480 nm originating from ThT was observed. Namely, it can be concluded that ThT from which fluorescent impurities are completely removed is obtained.

The invention claimed is:

1. A method for purifying pure thioflavin T, comprising:
   a step of preparing a thioflavin T solution in which crude thioflavin T is dissolved in a polar solvent;
   a step of carrying out liquid-liquid extraction of the thioflavin T solution with a non-polar solvent, and
   a step of measuring light emission intensity of the fluorescence of the thioflavin T solution which has a peak wavelength near 440 nm and determining whether or not the measured light emission intensity reaches the background level,
   wherein the polar solvent is an aqueous solvent,
   wherein the non-polar solvent is selected from the group consisting of hexane, heptane, octane, cyclohexane, toluene, xylene, and a mixture solvent consisting of two or more types thereof mixed with each other,
   wherein the thioflavin T concentration in the thioflavin T solution is within a range of 0.001 to 10 mmol/L, and
   wherein when it is determined that the measured light emission intensity does not reach the background level, the step of carrying out liquid-liquid extraction of the thioflavin T solution is repeated.

2. The method according to claim 1, wherein the liquid-liquid extraction step is carried out in a state in which light with a wavelength of 475 nm or lower is blocked.

3. A method for producing pure thioflavin T comprising a purification process for carrying out the method according to claim 1.

\* \* \* \* \*